United States Patent
Wagner et al.

(10) Patent No.: US 9,987,128 B2
(45) Date of Patent: Jun. 5, 2018

(54) INTRAOCULAR LENS INJECTOR

(71) Applicant: Santen Pharmaceutical Co., Ltd., Osaka-shi (JP)

(72) Inventors: Christian Winfried Wagner, Osaka (JP); Yoshitaka Yamada, Osaka (JP); Katsuyuki Ueno, Osaka (JP)

(73) Assignee: Santen Pharmaceutical Co., Ltd., Osaka (JP)

(*) Notice: Subject to any disclaimer, the term of this patent is extended or adjusted under 35 U.S.C. 154(b) by 214 days.

(21) Appl. No.: 14/655,787

(22) PCT Filed: Dec. 27, 2013

(86) PCT No.: PCT/JP2013/085039
§ 371 (c)(1),
(2) Date: Jun. 26, 2015

(87) PCT Pub. No.: WO2014/104271
PCT Pub. Date: Jul. 3, 2014

(65) Prior Publication Data
US 2015/0327992 A1 Nov. 19, 2015

(30) Foreign Application Priority Data
Dec. 27, 2012 (JP) .................. 2012-285823

(51) Int. Cl.
*A61F 2/16* (2006.01)

(52) U.S. Cl.
CPC ............ *A61F 2/1678* (2013.01); *A61F 2/167* (2013.01)

(58) Field of Classification Search
CPC ...... A61F 2/1678; A61F 2/167; A61F 2/1675; A61F 2/1691; A61F 9/0017
USPC ......................................... 606/107; 623/6.11
See application file for complete search history.

(56) References Cited

U.S. PATENT DOCUMENTS

| 7,156,854 B2 | 1/2007 | Brown et al. |
| 7,901,414 B2 | 3/2011 | Tourrette et al. |
| 8,603,103 B2 | 12/2013 | Kudo et al. |
| 2007/0050023 A1 | 3/2007 | Bessiere et al. |
| 2008/0058830 A1 | 3/2008 | Cole et al. |
| 2011/0046635 A1 | 2/2011 | Pankin et al. |
| 2011/0224677 A1 | 9/2011 | Niwa et al. |

(Continued)

FOREIGN PATENT DOCUMENTS

| CN | 101252895 A | 8/2008 |
| CN | 201235024 Y | 5/2009 |

(Continued)

*Primary Examiner* — Katherine M Shi
(74) *Attorney, Agent, or Firm* — The Webb Law Firm

(57) ABSTRACT

Provided is an intraocular lens injector that allows a haptic and a optic to be pushed in reliably. The intraocular lens injector includes a lens holder holding an intraocular lens which has a optic and a haptic extending in a curved shape from the optic, a device body to which the lens holder is attached, a plunger inserted projectably/retractably in the device body and coming into contact with the intraocular lens to push out this intraocular lens, and a nozzle portion connected to the device body, the nozzle portion releasing the intraocular lens while folding the intraocular lens concavely by a push-in operation of the plunger. A positioner is provided to push up the haptic along a thickness direction of the optic within a range contactable with a distal end of the plunger, when the lens holder and the intraocular lens are attached to the device body.

11 Claims, 9 Drawing Sheets

(56) References Cited

U.S. PATENT DOCUMENTS

| | | |
|---|---|---|
| 2011/0245840 A1 | 10/2011 | Seyboth et al. |
| 2012/0071888 A1 | 3/2012 | Putallaz et al. |
| 2012/0221102 A1 | 8/2012 | Tanaka et al. |

FOREIGN PATENT DOCUMENTS

| | | |
|---|---|---|
| CN | 102427777 A | 4/2012 |
| CN | 102843992 A | 12/2012 |
| EP | 2255751 A1 | 12/2010 |
| JP | 2004351196 A | 12/2004 |
| JP | 2005515807 A | 6/2005 |
| JP | 2007526091 A | 9/2007 |
| JP | 201145712 A | 3/2011 |
| WO | 2005084588 A1 | 9/2005 |
| WO | 2006070561 A1 | 7/2006 |
| WO | 2009012351 A2 | 1/2009 |
| WO | 2010028873 A1 | 3/2010 |
| WO | 2010064275 A1 | 6/2010 |
| WO | 2010079780 A1 | 7/2010 |
| WO | 2011048631 A1 | 4/2011 |

INTRAOCULAR LENS INJECTOR

CROSS-REFERENCE TO RELATED APPLICATIONS

This application is the United States national phase of International Application No. PCT/JP2013/085039 filed Dec. 27, 2013, and claims priority to Japanese Patent Application No. 2012-285823 filed Dec. 27, 2012, the disclosures of which are hereby incorporated in their entirety by reference.

BACKGROUND OF THE INVENTION

Technical Field

The present invention relates to an intraocular lens injector including a lens holder holding an intraocular lens which has an optic and a haptic extending in a curved shape from the optic, a device body to which the lens holder is attached, a plunger inserted projectably/retractably in the device body and coming into contact with the intraocular lens to push out this intraocular lens, and a nozzle portion connected to the device body, the nozzle portion releasing the intraocular lens while folding the intraocular lens concavely by a push-in operation of the plunger.

Background Art

Conventionally, as one method of cataract surgery, there has been commonly implemented a method of treating by removing a clouded natural crystalline lens from the eye and then inserting an artificial intraocular lens into the eye. For the insertion of the intraocular lens into the eye, an insertion instrument called an injector is employed. This injector includes an instrument body having a placing portion on which the intraocular lens is to be placed and a nozzle portion releasing the intraocular lens while folding the intraocular lens concavely, and a plunger coming into contact with the intraocular lens to push out this intraocular lens (e.g. Patent Document 1).

The above injector further includes a slider configured to come into contact with the intraocular lens to advance this lens prior to start of a push-in operation of the plunger. In this slider, there is formed a sloped face, such that in association with an advancing operation of the slider, the haptic is pushed up along the sloped face thereof. In the course of this, the intraocular lens pushed by the slider is in contact with an inner face of the nozzle portion and the haptic is fixed at the position of its root.

Next, when the plunger is pushed in, the distal end of the plunger comes into contact with the haptic. With this, the haptic as receiving the pressing force from the plunger is deformed in the push-in direction of the plunger and is moved to a region upwardly of the optic. The haptic, as its deformation at the root being regulated, will be bent and deformed from the vicinity of the center of the haptic and the distal end portion of the haptic will be placed to be overlapped with the top portion of the optic.

CITATION LIST

Patent Literature

Patent Document 1: WO2010/079780 Publication

SUMMARY OF THE INVENTION

Technical Problem

As described above, since the conventional injector includes a slider for pushing up the haptic, an advancing operation of the slider is needed prior to start of push-in operation of the plunger. Therefore, the operation for an operator is troublesome. Further, due to increase in the number of components constituting the injector, manufacturing costs too will increase.

Moreover, when the haptic is pushed in by the plunger, a portion of this haptic distant from the root is pushed. For this reason, there is possibility of the haptic being deformed in an unexpected direction by its elasticity, whereby the haptic may be moved away from the distal end of the plunger. If the plunger is pushed in under this condition, the haptic may be moved freely to be inadvertently entrapped e.g. between the plunger and the nozzle portion for instance, thus being damaged.

The present invention has been made in view of the above-described background art and the object of the invention is to provide an intraocular lens injector which allows a haptic and an optic to be pushed in a reliable manner.

Solution to Problem

An intraocular lens injector relating to this disclosure comprises:

a lens holder holding an intraocular lens which has an optic and a haptic extending in a curved shape from the optic;

a device body to which the lens holder is attached;

a plunger inserted projectably/retractably in the device body and coming into contact with the intraocular lens to push out this intraocular lens;

a nozzle portion connected to the device body, the nozzle portion releasing the intraocular lens while folding the intraocular lens concavely by a push-in operation of the plunger; and a positioner pushing up the haptic along a thickness direction of the optic within a range contactable with a distal end of the plunger when the lens holder and the intraocular lens are attached to the device body, the positioner being provided in distribution in the device body and in the lens holder.

In order to prevent damage to the haptic, it is important that in the course of a push-in operation of the plunger, the haptic be overlapped with one side of the optic, and the optic and the haptic be in appropriate contact with the distal end portion of the plunger. With realization of this condition, the intraocular lens will be folded with the haptic being enclosed by the optic, whereby inadvertent entrapment of the haptic e.g. between the plunger and the nozzle portion and damage thereby can be prevented.

With the positioner configured as above, when the lens holder is attached to the device body, the haptic will be offset along the thickness direction of the optic. As a result, the optic and the haptic can come into contact with different positions of the distal end portion of the plunger. Thus, it is possible to prevent occurrence of such inconvenience of the haptic becoming inadvertently entrapped between the distal end portion of the plunger and the optic for instance.

In this way, with provision of the positioner in distribution in the device body and in the lens holder, there is no need to provide separately a member for pushing up the haptic. Moreover, as the operation of pushing up the haptic is extremely simple, the operational load on an operator can be alleviated. Further, the number of components is reduced, so that the manufacturing costs too can be reduced.

In addition, in the injector having the above configuration, the haptic is deformed immediately before a push-in operation of the plunger. Therefore, no plastic deformation will remain in the haptic after placement of the intraocular lens in the eye, either.

In the intraocular lens injector according to this disclosure, preferably, the positioner includes a convex portion protruding from a bottom portion of the device body and having an end face pushing up the haptic at the time of attachment of the lens holder and the intraocular lens to the device body, and an inserting portion provided in the lens holder to avoid interference with the convex portion.

With the above-described arrangement, by an operation of assembling the lens holder to the device body from above, a push-up operation of the haptic by the convex portion can be effected simultaneously. Further, since the convex portion protrudes from the bottom portion of the device body, the direction of assembling the lens is in agreement with the direction for displacing the haptic, so that the push-up of the haptic can be realized with a simple component.

In the intraocular lens injector according to this disclosure, preferably, the lens holder includes a guiding portion coming into contact with the haptic to determine a movement direction of the haptic in the course of the push-in operation of the plunger.

Thanks to the positioner, the haptic and the optic are set at appropriate positions relative to the distal end portion of the plunger. However, when e.g. the push-in force from the plunger is applied to the haptic, the intraocular lens may be rotated inadvertently and the haptic may move in an unexpected direction. As a result, it becomes impossible for the plunger to push the intraocular lens and the haptic simultaneously.

With the above-described arrangement, however, even if such rotation of the intraocular lens should start, the haptic comes into contact with the guiding portion formed in the lens holder, so that further movement of the haptic can be prevented. Consequently, the contact state between the plunger and the haptic can be maintained favorably, so that the haptic and the optic can be pressed in, with keeping the haptic overlapped with one lateral face side of the intraocular lens.

In the above-described configuration, preferably, the guiding portion is provided in the form of a wall on a lateral side of the plunger and extending between a position where a distal end portion of the haptic is located under an initial condition of the intraocular lens being attached to the lens holder and a position where the distal end portion of the haptic moves when the plunger is pushed in to come into contact with the intraocular lens.

With the above-described arrangement of providing a guiding portion in the form of a wall, during push-in of the haptic by the plunger, the distal end portion of the haptic can constantly be kept in contact with the wall-like guiding portion. Therefore, until the plunger comes into contact with the intraocular lens, the distal end portion of the plunger keeps pressing a substantially same position in the haptic. Accordingly, no inadvertent deformation will occur in the haptic and the haptic can be guided to an appropriate position relative to the intraocular lens.

In the above-described configuration, preferably, at least in a portion of the guiding portion, there is provided a sloped wall portion extending progressively away from the plunger toward a far side along a push-in direction of the plunger.

When the haptic is pushed in by the plunger, the haptic will tend to be deformed around its proximal end portion protruding from the optic. As a result, a particular portion in the haptic which has been placed in contact with the distal end portion of the plunger may move toward the side opposite the proximal end portion in association with further push-in operation of the plunger. This movement does not involve any rotation of the intraocular lens, but is based on natural bending deformation of the haptic. In association with this, the distal end portion of the haptic too will move to the side away from the proximal end portion. The sloped wall portion configured as above is provided for appropriately guiding this movement of the distal end portion of the haptic. The angle and the length of this sloped wall portion will be set appropriately in accordance with the length and/or hardness of the haptic. With this, it becomes possible to cause the haptic to be bent and deformed appropriately in its overall area from its proximal end portion to its distal end portion, during the push-in operation of the plunger, with effective prevention of rotation of the intraocular lens. Consequently, the push-in operation of the haptic and the optic by the plunger can proceed in a more reliable manner.

In the above-described configuration, preferably, in the guiding portion, there is formed, along a push-in direction of the plunger, a stepped portion by which the distal end portion of the haptic is placed on the side away from a bottom portion of the device body, relative to a thickness-wise center position of the optic.

With the above-described formation of a stepped portion, in the course of push-in operation of the plunger, it is possible to prevent the distal end portion of the haptic from being bent/deformed especially toward the back side of the optic. Therefore, in the course of push-in operation of the plunger, the haptic can be reliably guided to the front face of the intraocular lens, that is, the face of the intraocular lens whose haptic is to be enclosed by the optic at the time of folding of the intraocular lens.

DETAILED DESCRIPTION OF THE INVENTION

Next, embodiments of an intraocular lens injector 1 relating to this disclosure will be explained with reference to the accompanying drawings. It should be noted however that the present disclosure is not limited to these embodiments, but can be modified in various ways as long as such modifications do not deviate from the essence thereof.

1. General Configuration

Figure 1:
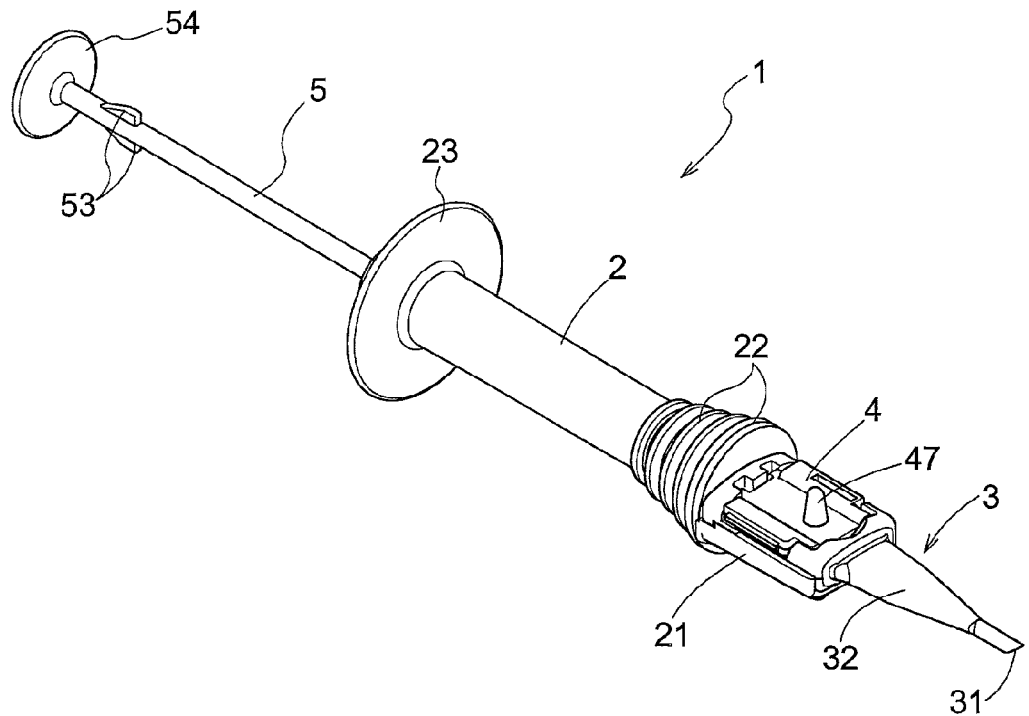
FIG. 1 is an overall view of an intraocular lens injector.

FIG. 1 shows an overall view of an intraocular lens injector 1 ("injector 1" hereinafter) according to this embodiment. This injector 1 includes a cylindrical device body 2, a distal end tip 3 having a nozzle portion 32 to be connected to the device body 2, a lens holder 4 attachable to the device body 2, and a bar-like plunger 5 inserted in the device body 2. An intraocular lens 7 includes an optic 7a as a substitute implant for a natural crystalline lens, and a pair of front and rear haptics 7b and 7c extending in a curved shape from the optic 7a and this intraocular lens 7 is held in the lens holder 4. Incidentally, in the instant embodiment, there is shown one example of such intraocular lens 7 of a one-piece type, having the optic 7a and the pair of haptics 7b, 7c formed integrally with each other.

In the following discussion, explanation will be given with referring the axial direction of the plunger 5 as a front/rear direction, the directions perpendicular to the axis as the upper/lower, right/left directions.

2. Device Body

Figure 2:
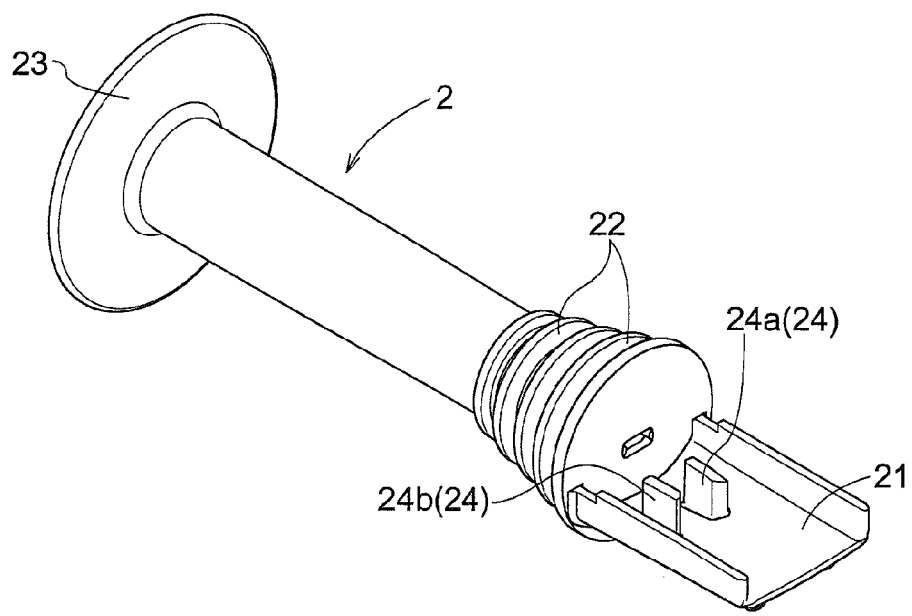
FIG. 2 is a perspective view showing a device body in a first embodiment.
Figure 4:
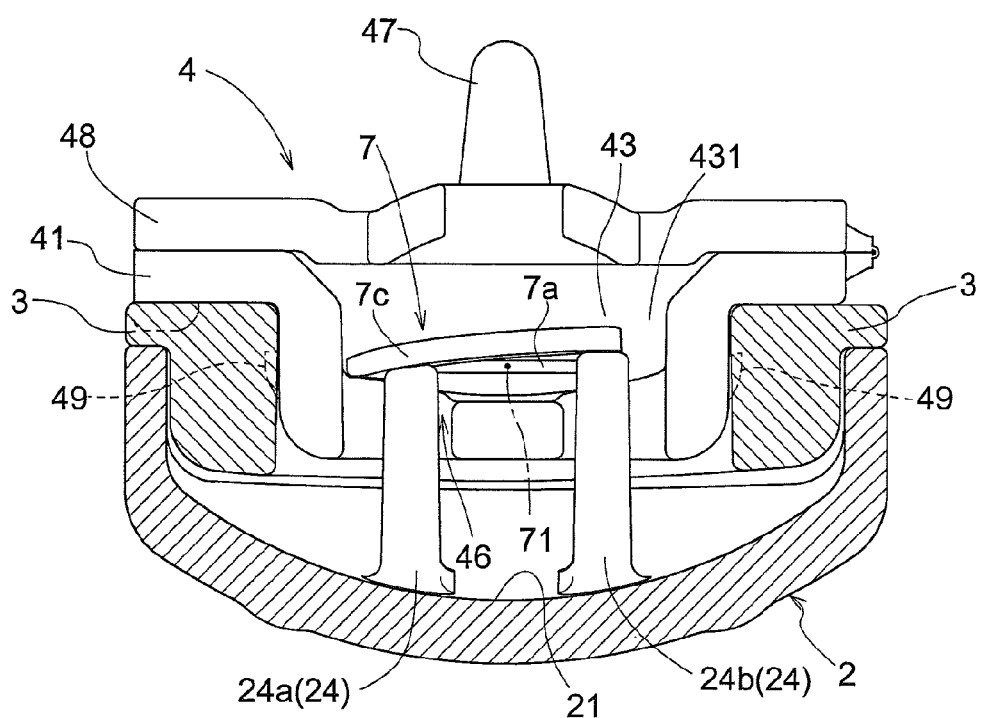
FIG. 4 is a side view showing a device body and the lens holder in the first embodiment.
Figure 5:
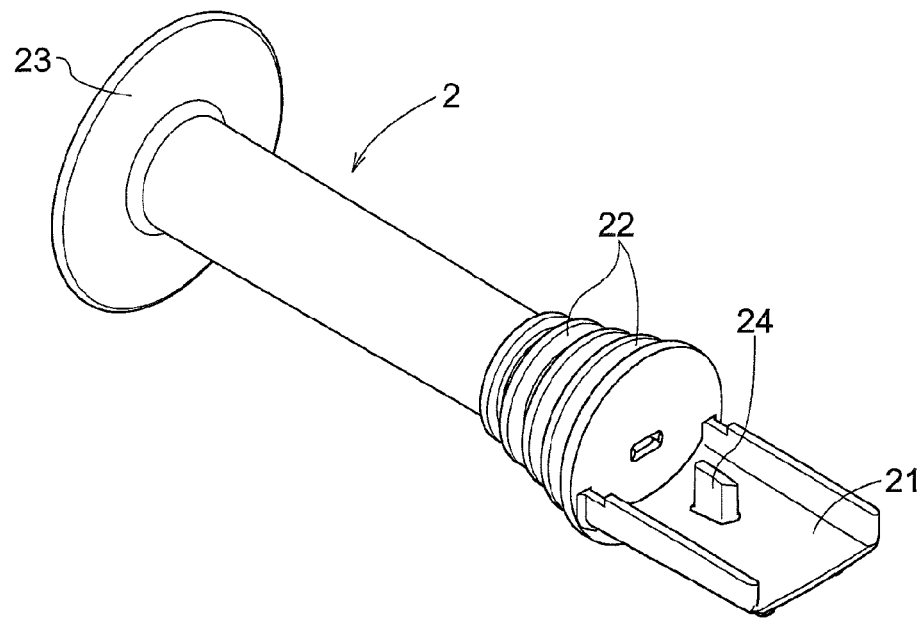
FIG. 5 is a perspective view showing a device body in a second embodiment.
Figure 7:
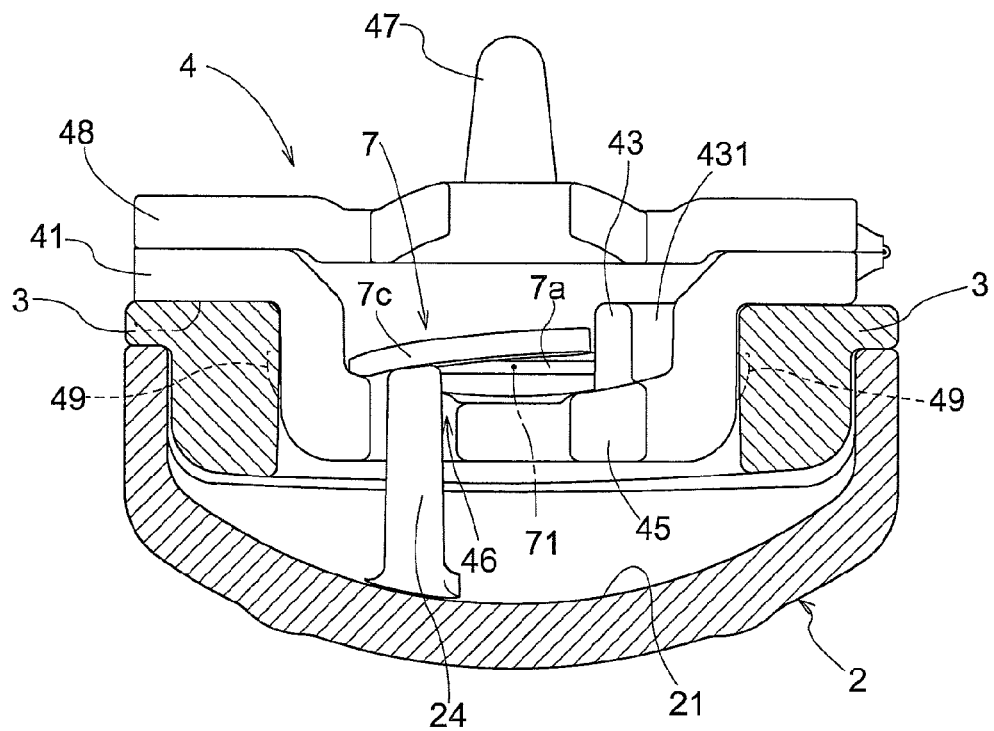
FIG. 7 is a side view showing the device body and the lens holder in the second embodiment.

FIG. 2 and FIG. 5 show perspective views of the device body 2. FIG. 4 and FIG. 7 shown side views showing a condition of the lens holder 4 being set to the device body 2.

The device body 2 includes a bottom portion 21 provided on the front side thereof for allowing engagement thereto of the distal end tip 3 and the lens holder 4, a plurality of annular protruding portions 22 provided on an outer face at the front end thereof to be gripped by an operator, and a flange-like holding portion 23 provided in the outer face at the rear end to be held by the operator by hooking his/her fingers thereon. The device body 2 is formed with using a resin having shock resistance such as polycarbonate.

Incidentally, the annular protruding portions 22 and the holding portion 23 can be shaped in any way as long as the requisite functions thereof can be achieved. For instance, the holding portion 23 can be formed like a projection that allows finger hooking, rather than the flange-like shape.

In operation, the operator will push-in the plunger 5 by one hand and will grip the annular protruding portions 22 by the other hand, thereby to release the intraocular lens 7 into a patient's eye in the order of succession of the front haptic 7b, the optic 7a and then the rear haptic 7c. The provision of the annular protruding portions 22 facilitates the operator's gripping of the injector 1, thus providing improvement of the maneuverability of the injector 1.

As shown in FIG. 2 and FIG. 5, on the bottom portion 21, there are formed convex portions 24 protruding upwards to be inserted to an inserting portion 46 of the lens holder 4. When the lens holder 4 in which the intraocular lens 4 is set in advance is attached to the device body 2 from the upper side thereof, as shown in FIG. 4 and FIG. 7, the convex portions 24 will be inserted to the inserting portion 46 of the lens holder 4. In this, the rear haptic 7c is pushed up by as coming into contact with the upper end faces of the convex portions 24 to be displaced upwards from a thickness-wise center position 71 of the optic 7a. The rear haptic 7c and the optic 7a are placed upwards and downwards respectively along the thickness direction of the optic 7a and will be fixed in position at positions contactable by a distal end portion 51 of the plunger 5 and the rear haptic 7c. In this way, the convex portions 24 and the inserting portion 46 together constitute a positioner for pushing up the rear haptic 7c along the thickness direction of the optic 7a within a range contactable with the distal end portion 51 of the plunger 5.

On the other hand, although it is conceivable to hold the intraocular lens 7 to the lens holder 4 by pushing up the rear haptic 7c in advance, there is possibility of the rear haptic 7c failing to return to its original shape after long-term storage of the intraocular lens 7 in the lens holder 4. However, with the provision of the convex portion 24 in the device body 2, it is possible to displace the rear haptic 7c immediately before push-in operation of the plunger 5. Therefore, there will remain no plastic deformation in the rear haptic 7c after placement of the intraocular lens 7 within the eye.

Incidentally, the intraocular lens 7 can be set in the lens holder 4 attached to the device body 2. With setting of the intraocular lens 7 to the lens holder 4, the rear haptic 7c will be pushed up as coming into contact with the upper end faces of the convex portions 24 and set at a position contactable by the distal end portion 51 of the plunger 5 and the rear haptic 7c. Further, the shape of the convex portion 24 can vary in any desired way, as long as it can come into contact with the rear haptic 7c to push this portion 7c up.

3. Lens Holder

Figure 3:
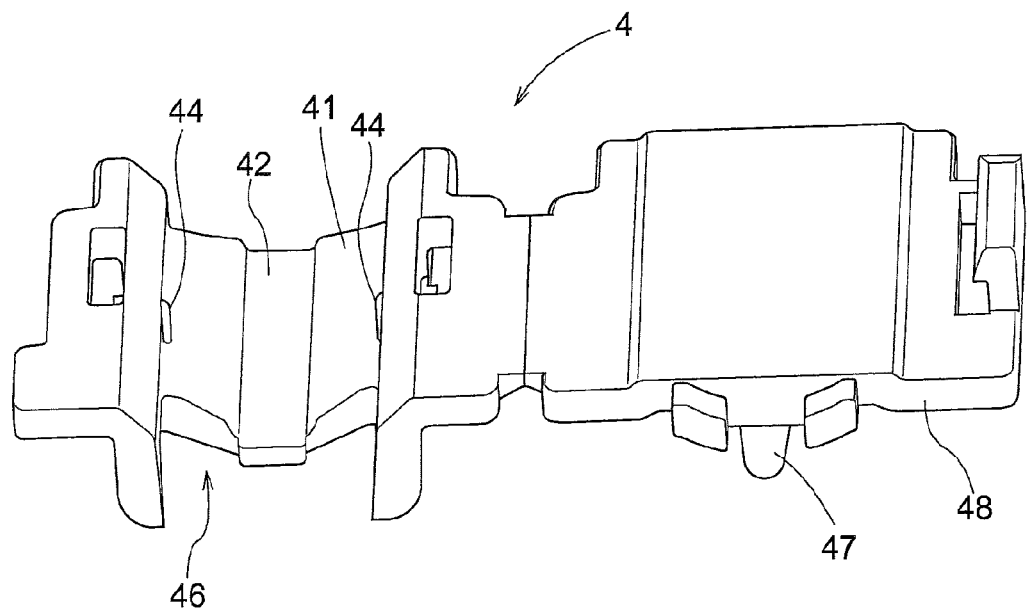
FIG. 3 is a perspective view showing a lens holder in the first embodiment.
Figure 6:
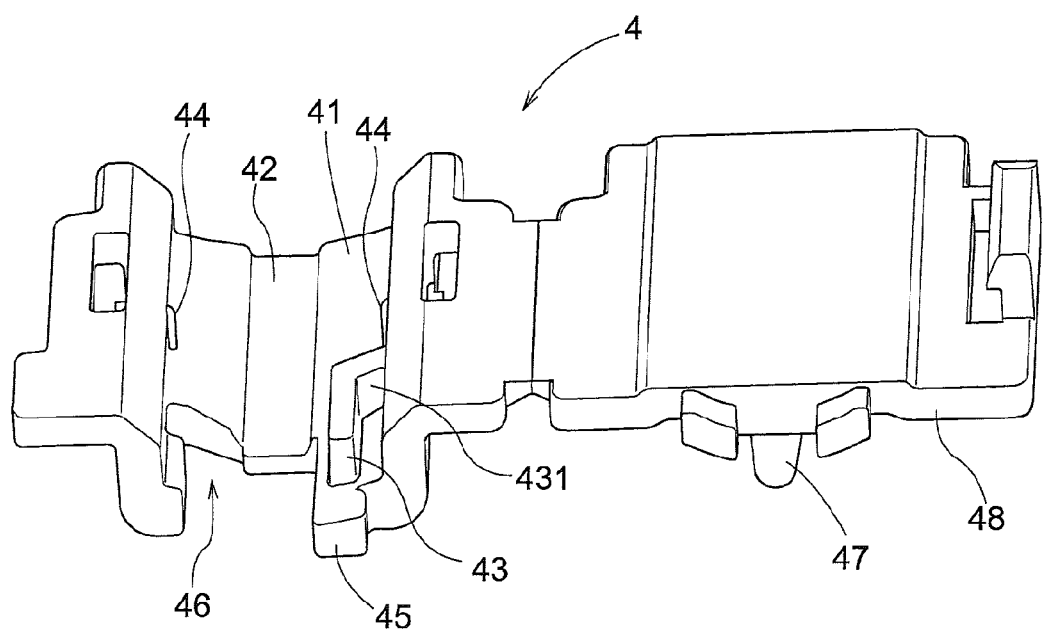
FIG. 6 is a perspective view showing a lens holder in the second embodiment.

FIG. 3 and FIG. 6 show perspective views of the lens holder 4. The lens holder 4 includes a bottom portion 41 on which the intraocular lens 7 is to be placed, and a lid portion 48 connected to the bottom portion 41 and openable/closable. After placement of the intraocular lens 7 on the bottom portion 41, the lid portion 48 is closed, thus holding the intraocular lens 7. The lens holder 4 is formed of using a resin having chemical resistance such as polypropylene.

When the intraocular lens 7 is to be stored in sterile distilled water, it will suffice to store the lens holder 4 alone in a container containing sterile distilled water. Thus, discomfort to the operator touching a wet container can be alleviated and convenience can be improved, in comparison with a situation of the entire injector being wetted in liquid.

The bottom portion 41 of the lens holder 4 includes a groove portion 42 formed at the center thereof and extending along the front/rear direction, side protrusions 44 protruding from the lateral sides, and the inserting portion 46 formed by cutting away the rear end. Movement of the plunger 5 occurs along the groove portion 42, with its advancing direction kept constant.

Incidentally, the shape of the inserting portion 46 can vary in desired manner as long as it can avoid interference with the convex portions 24. For instance, hole portions can be formed at positions in the bottom portion 41 where the convex portions 24 are inserted.

Further, on the outer face of the bottom portion 41, there are provided retaining pawls 49 engageable with engaging hole portions 39 of the distal end tip 3.

Further, there is provided a grip portion 47 protruding from the outer face of the lid portion 48. When the lens holder 4 is to be assembled to the device body 2 from the upper side thereof, the operation is possible with gripping the grip portion 47. Thus, operational ease is provided.

Incidentally, the shape of the gripping portion 47 can vary in desired manner. Also, the gripping portion 47 can be omitted in case the intraocular lens 7 is to be set to the injector 1 having the lens holder 7 attached to the lens body 2 in advance.

4. Plunger

Figure 8:
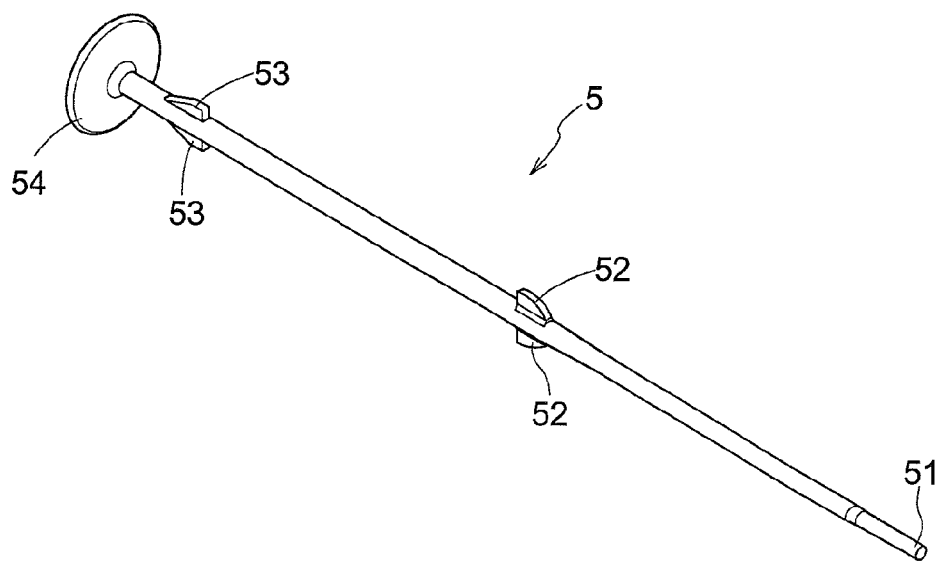
FIG. 8 is a perspective view of a plunger.

FIG. 8 shows a perspective view of the plunger 5. The plunger 5 includes the distal end portion 51 having a flat face for coming into contact with the intraocular lens 7, retaining portions 52 to be retained by the rear end of the device body 2, stoppers 53 formed at the rear side and protruding to the outside, and a flange-like pushing portion 54 provided rearwardly of the stoppers 53. The plunger 5 is formed with using a resin having shock resistance such as polycarbonate.

Incidentally, the shapes of the distal end portion 51, the stoppers 53 and the pushing portion 54 can vary in any way as long as the requisite functions thereof can be achieved. For instance at upper and lower opposed ends of the distal end portion 51, small projections or the like for clamping the intraocular lens 7 can be provided.

Further, as an alternative, an elastic element (not shown) such as a spring can be provided along the outer circumference face of the plunger 5 on its side closer to the distal end portion 51 than the retaining portions 52 and the inner circumference face of the device body 2. With this arrangement, the push-in operation of the plunger 5 will encounter a reaction force from the elastic element, so that uncontrolled sudden release of the intraocular lens 7 from the distal end portion 51 of the plunger 5 can be prevented. The disposing position of such elastic element is not particularly limited. For instance, the element can be disposed also between the pushing portion 54 of the plunger 5 and the rear end of the device body 2. Any other arrangement will be possible as long as the push-in operation of the plunger 5 will encounter a reaction force from the elastic element.

The plunger 5 will be inserted into the device body 2 from the rear side thereof and as the retaining portions 52 come to be retained by the rear end of the device body 2, the plunger 5 will be set at the position contactable by the rear haptic 7c raised by the positioner and the distal end portion 51.

Further, an arrangement is provided such that in the course of push-in operation of the plunger 5, with advancing of the intraocular lens 7 in the inside of the nozzle portion 32, a contact force between the inner surface of the distal end tip 3 and the optic 7a will increase progressively. As this arrangement causes progressive reduction in the advancing speed of the plunger 5, uncontrolled sudden release of the intraocular lens 7 can be prevented.

On the other hand, upon release of the intraocular lens 7 to the outside, the elastic force of this intraocular lens 7 is released, which force would promote quickened advancing of the plunger 5 to the front side. However, the stoppers 53 are configured to protrude largely so as to be stopped at the rear end of the device body 2, the movement of the plunger 5 is stopped at a push-in completion position. For this reason, no adjusting in the pushing force is required from the operator and accidental contact of the distal end portion 51 with the intraocular tissue due to sudden uncontrolled advancement of the plunger 5 upon release of the elastic force of the intraocular lens 7 can be prevented in a reliable manner. Moreover, it is also possible to visually confirm the push-in completion position by viewing the stoppers 53. So, there is no need for the operator to carry out the operation while constantly checking the position of the distal end portion 51 of the plunger 5.

5. Distal End Tip

Figure 9:
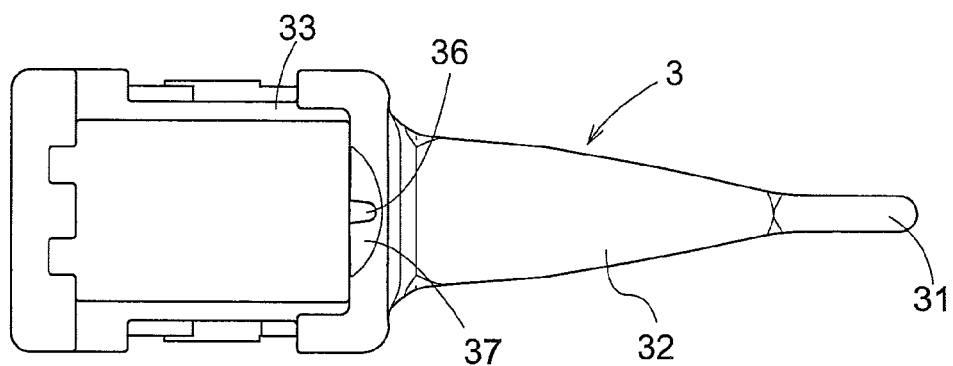
FIG. 9 is a plane view showing a distal end tip.
Figure 10:
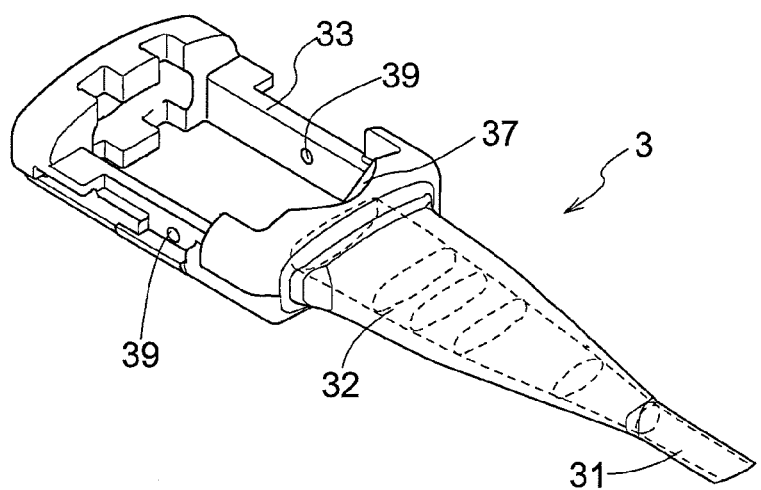
FIG. 10 is a perspective view showing the distal end tip.

FIG. 9 and FIG. 10 show a plane view and a perspective view of the distal end tip 3. The distal end tip 3 includes a releasing portion 31 for releasing the intraocular lens 7, a nozzle portion 32 having an inner diameter which increases progressively toward the front side, and a rectangular portion 33 having an aperture at the center thereof and having a rectangular outer circumference. As the rectangular portion 33 is engaged with the receiving portion 21 of the device body 2, the nozzle portion 32 is connected to the device body 2.

Incidentally, the mode of engagement between the distal end tip 3 and the device body 2 can vary in any desired manner, such as engagement between a retaining pawl and a retaining hole, for instance. The distal end tip 3 is formed with using a resin having chemical resistance and softness, such as polyamide.

Figure 13:
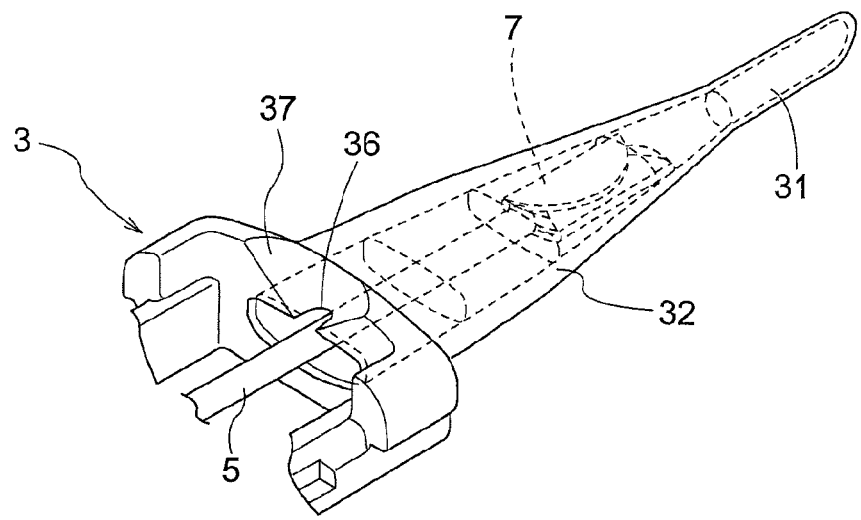
FIG. 13 is a perspective view showing a condition of an intraocular lens passing through a nozzle portion.

The intraocular lens 7 will be pushed by the plunger 5 and progressively folded as it is passed in the inside of the nozzle portion 32. In this, since the rear haptic 7c is disposed at the region upwardly of the optic 7a by the positioner, the rear haptic 7c is enclosed by the optic 7a as illustrated in FIG. 13. Next, the intraocular lens 7 under the folded state will reach the releasing portion 31. The intraocular lens 7 having reached the releasing portion 31 will be inserted through the cut side of the releasing portion 31, into the eye in the successive order of the front haptic 7b, the optic 7a and the rear haptic 7c.

The rectangular portion 33 includes engaging hole portions 39 engageable with retaining pawls 49 of the lens holder 4, and includes, on the front side thereof, an injection hole portion 36 through which an amount of elasto-viscous substance such as hyaluronate sodium can be injected with use of a syringe and an injection recess portion 37 formed around the injection hole portion 36.

Incidentally, it is also possible to configure such that the retaining pawls 49 of the lens holder 4 are directly engaged with the bottom portion 21 of the device body, without providing the engaging hole portions 39 in the distal end tip 3.

At the time of use of the injector 1, the lens holder 4 will be inserted into the aperture of the rectangular portion 33. In this, as the front and rear portions of the rectangular portion 33 of the distal end tip 3 are formed asymmetric, the operator can carry out the inserting operation without erring in the setting direction of the lens holder 4. Further, when a needle of the syringe is inserted into the injection hole portion 36, the distal end of this syringe needle is guided by the injection recess portion 37. Therefore, the injection of the elasto-viscous substance can proceed in a reliable manner.

Positioner

First Embodiment

In this embodiment, as shown in FIGS. 2-3, on the bottom portion 21 of the device body 2, there are provided the convex portions 24 protruding therefrom whereas the inserting portion 46 formed by cutting away the rear end of the bottom portion 41 of the lens holder 4 is formed along the right and left lateral walls. The convex portions 24 comprise a first convex portion 24a for pushing up the proximal end portion of the rear haptic 7c and a second convex portion 24b having a greater protrusion amount than the first convex portion 24a and configured for pushing up the distal end portion of the rear haptic 7c. Namely, the positioner for pushing up the rear haptic 7c is comprised of the first convex portion 24a, the second convex portion 24b, and the inserting portion 46.

Figure 11:
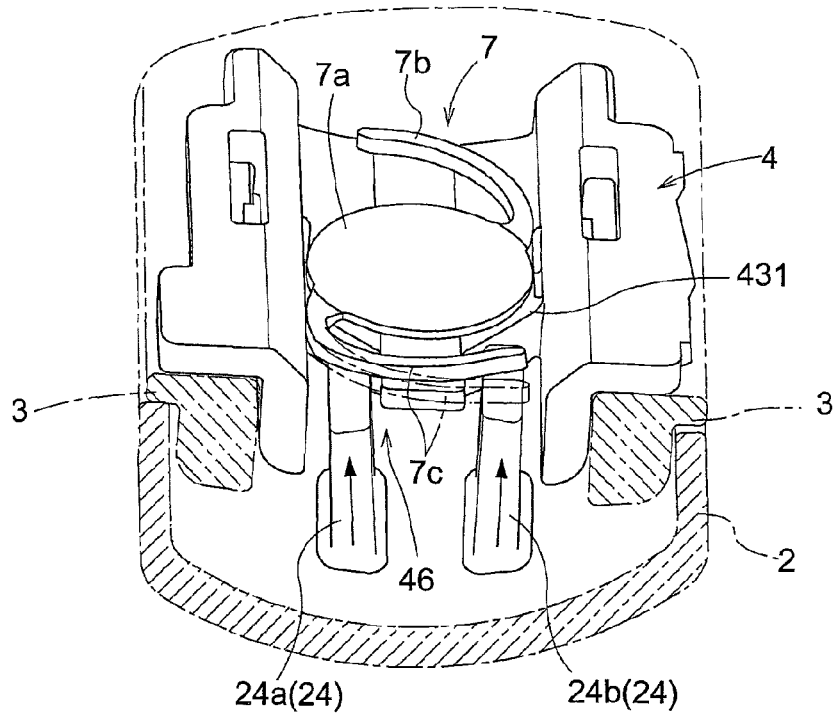
FIG. 11 is a perspective view showing a condition before a plunger is pushed in the first embodiment.
Figure 12:
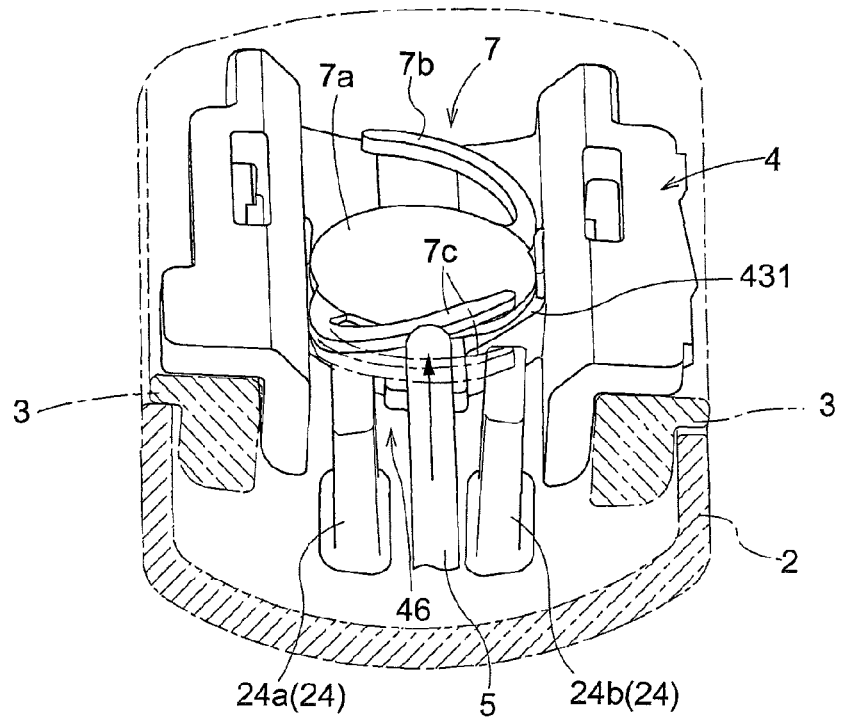
FIG. 12 is a perspective view showing a condition after the plunger is pushed in the first embodiment.

With reference to FIGS. 11-13, there will be explained a manipulation of the intraocular lens 7 by a push-in operation of the plunger 5. FIG. 11 is a perspective view showing the initial condition where the intraocular lens 7 is attached to the lens holder 4. FIG. 12 is a perspective view showing a condition when the plunger 5 comes into contact with the intraocular lens 7. FIG. 13 is a perspective view showing a condition when the intraocular lens 7 is passing through the nozzle portion 32.

As shown in FIG. 11, when the lens holder 4 and the intraocular lens 7 are mounted to the device body 2, the first convex portion 24a pushes up and supports the proximal end portion of the rear haptic 7c and the second convex portion 24b pushes up and supports the distal end portion of the rear haptic 7c. As a result, the rear haptic 7c is offset along the thickness direction of the optic 7a. Next, as shown in FIG. 12, when the plunger 5 is pushed in, the vicinity of the center of the rear haptic 7c is pressed by the distal end portion 51. With progress of this push-in operation, there is realized a condition where the rear haptic 7c is disposed at a region upwardly of the optic 7a and the optic 7a and the rear haptic 7c are in appropriate contact with the distal end portion 51 of the plunger 5 respectively.

In the above, the posture of the rear haptic 7c is stabilized as its opposed ends are pushed up and supported by the first convex portion 24a and the second convex portion 24b. Namely, there will occur no such inconvenience of the contact state with the distal end portion 51 of the plunger 5 being inadvertently released due to sagging (dropping) of the distal end portion of the rear haptic 7c. Moreover, in the instant embodiment, since the rear haptic 7c is supported by the two faces, i.e. the upper end faces of the first convex portion 24a and the second convex portion 24b, the rear haptic 7c can be moved in a stable manner in association with a push-in operation of the plunger 5.

Next, with progress of the push-in operation of the plunger 5, as shown in FIG. 13, as the intraocular lens 78 passes through the inside of the nozzle portion 32, the intraocular lens 7 is folded concavely so that the rear haptic 7c is enclosed by the optic 7a. For this reason, the rear haptic 7c will not be inadvertently entrapped between the lateral face of the plunger 5 and the inner face of the distal end tip 3, whereby damage of the rear haptic 7c can be prevented. Accordingly, after setting of the intraocular lens 7 in the eye, the optic 7a and the pair of haptics 7b, 7c will return to their original states.

Positioner and Guiding Portion

Second Embodiment

In this embodiment, as shown in FIGS. 5 and 6, one convex portion 24 in the form of a protrusion is provided on the left side on the bottom portion 21 of the device body 2, whereas at the rear end of the bottom portion 41 of the lens holder 4, there is formed an inserting portion 46 by cutting away the rear end from the left lateral wall to vicinity of the center portion. Further, in the lens holder 4, there is provided a wall portion 43 (an example of "a guiding portion") which protrudes upwards from the bottom portion 41. This wall portion 43 includes, on the front side thereof, a bent portion 431 bent to the outer side. Therefore, during transport of the lens holder 4 in which the intraocular lens 7 is mounted in advance, the side protrusions 44 and the bent portion 431 prevent movement of the intraocular lens 7 in the front/rear and right/left directions, so the set position of the intraocular lens 7 can be fixedly maintained.

Figure 14:
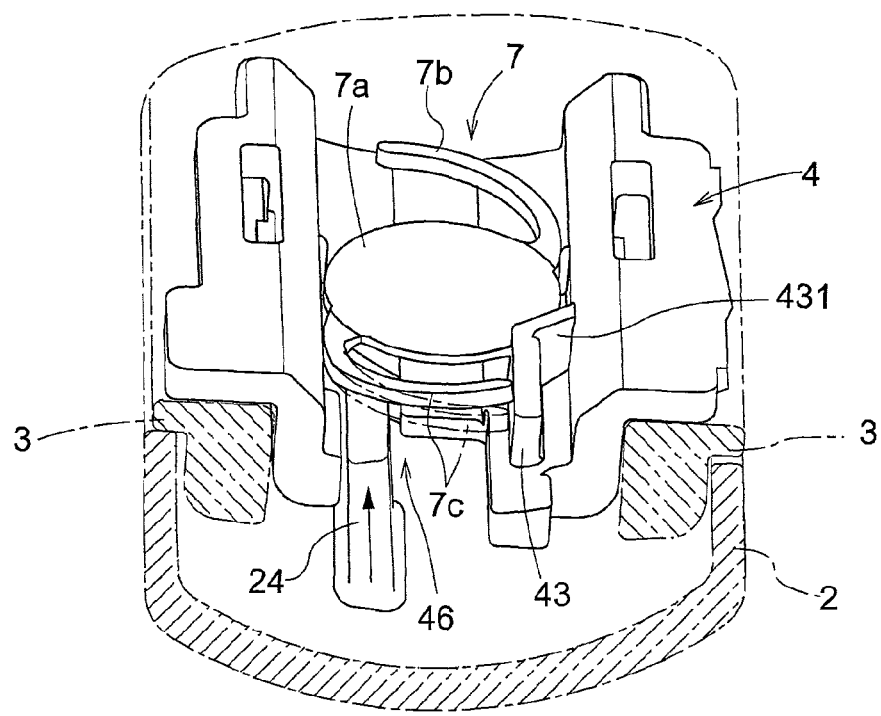
FIG. 14 is a perspective view showing a condition before a plunger is pushed in the second embodiment.
Figure 15:
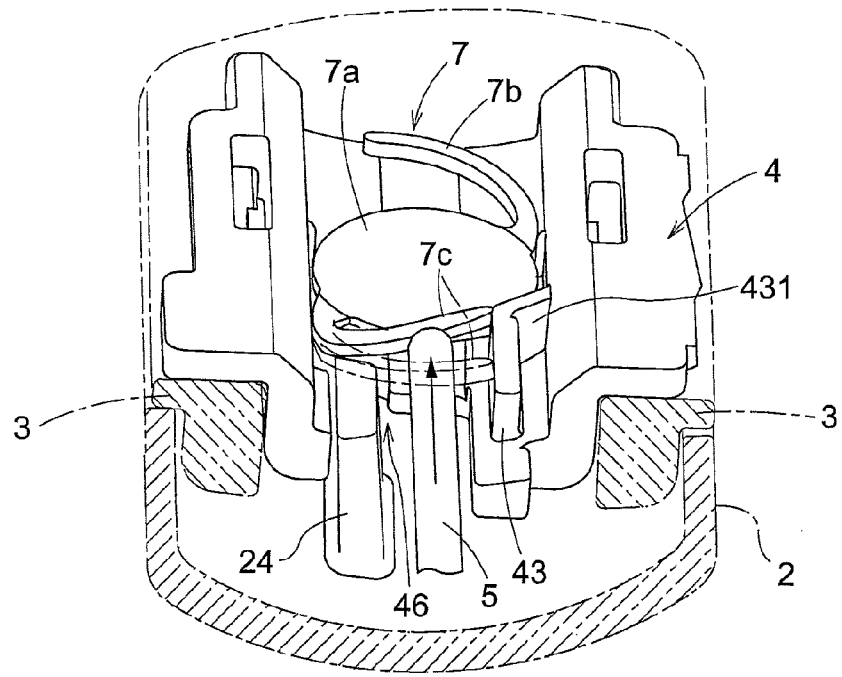
FIG. 15 is a perspective view showing a condition after the plunger is pushed in the second embodiment.

With reference to FIGS. 14-15, there will be explained a movement of the intraocular lens 7 by a push-in operation of the plunger 5. FIG. 14 is a perspective view showing the initial condition where the intraocular lens 7 is attached to the lens holder 4. FIG. 15 is a perspective view showing a condition when the plunger 5 comes into contact with the intraocular lens 7.

As shown in FIG. 14, by means of the positioner comprised of the convex portion 24 and the inserting portion 46, the rear haptic 7c is pushed up within a range of keeping contact between the distal end portion 51 of the plunger 5 and the rear haptic 7c, and the lateral face of the wall portion 43 formed like a wall on the lateral side of the plunger 5 and the distal end portion of the rear haptic 7c come into contact with each other. Next, when the plunger 5 is pushed in, the vicinity of the center of the rear haptic 7c is pressed by the distal end portion 51.

In the above, if the wall portion 43 were absent to allow free movement of the rear haptic 7c, the rear haptic 7c could skid sideways to the outer side from the distal end portion 51 of the plunger 5. As a result, in association with such sideway skidding displacement of the rear haptic 7c, the intraocular lens 7 would be rotated counterclockwise. And, with such rotation of the intraocular lens 7, at the time of contact between the plunger 5 and the intraocular lens 7, the distal end portion 51 of the plunger 5 would come into contact with the root portion of the rear haptic 7c or would come into contact with the optic 7a alone without coming into contact with the rear haptic 7c. And, if the push-in operation of the plunger 5 proceeded under this condition, a crack could be created at the root portion of the rear haptic 7c under the pressing force from the plunger 5, or the rear haptic 7c not contacting the distal end portion 51 of the plunger 5 would come into sliding contact with the inner face of the nozzle portion 32, thus being extended in the direction opposite to the push-in direction, so that the curved shape could not be maintained and deformation would tend to occur. Further, since the rear haptic 7c is located outside the optic 7a, with progress of the push-in operation of the plunger 5, there could occur inconvenience of the rear haptic 7c being inadvertently entrapped between the plunger 5 and the nozzle portion 32, thus being damaged, without being enclosed by the optic 7a folded concavely inside the nozzle portion 32.

On the other hand, in the instant embodiment, since the distal end portion of the rear haptic 7c comes into contact with the lateral face of the wall portion 43 acting as restricting end, the direction of movement of the rear haptic 7c is fixedly determined. That is, in association with a push-in operation of the plunger 5, the rear haptic 7c is moved along the push-in direction of the plunger 5. Therefore, as illustrated in FIG. 15, the rear haptic 7c will be disposed in a region upwardly of the optic 7a and the distal end portion 51 of the plunger 5 will come into contact with the optic 7a and the rear haptic 7c.

In this way, since the wall portion 43 is provided in the form of a wall beside the plunger 5 extending between the position where the distal end portion of the rear haptic 7c is located under the initial condition of the intraocular lens 7 being mounted in the lens holder 4 and the position to which the distal end portion of the rear haptic 7c has moved as the result of the push-in operation of the plunger 5 until its contact with the intraocular lens 7. Thus, in the course of push-in operation of the plunger 5, the wall portion 7 comes into contact with the rear haptic 7c to determine the direction of movement of this rear haptic 7c.

Alternative Embodiment 1

Figure 16:
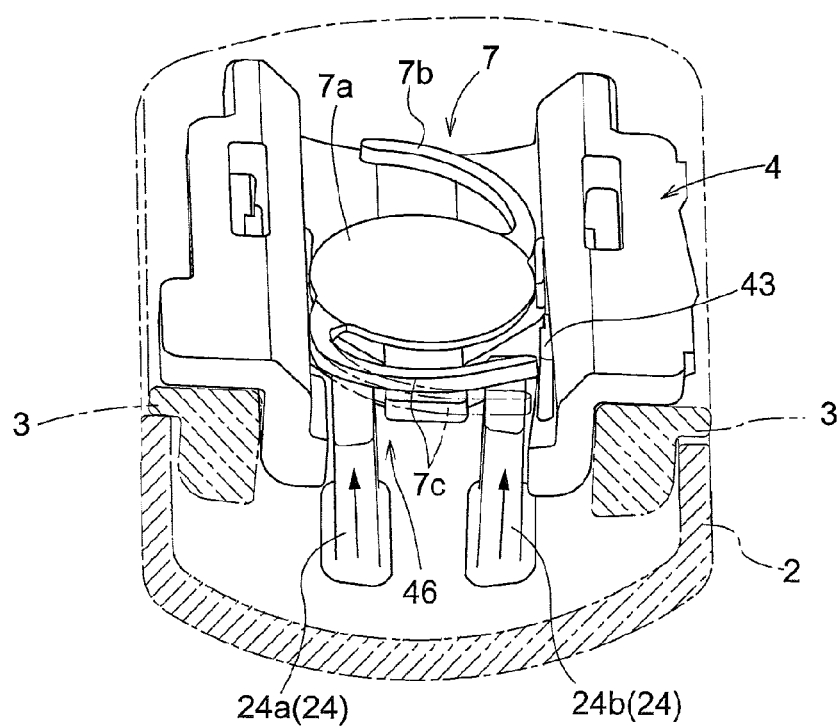
FIG. 16 is a perspective view showing a lens holder in a first alternative embodiment.

As shown in FIG. 16, in addition to the configuration of the first embodiment, a wall portion 43 (an example of "a guiding portion") is provided to protrude upwards from the bottom portion 41 of the lens holder 4. In this case, in addition to the positioner provided in the first embodiment, since the distal end portion of the rear haptic 7c comes into contact with the lateral face of the wall portion 43 acting as restricting end, the direction of movement of the rear haptic 7c is fixedly determined. Accordingly, rotation of the intraocular lens 7 can be prevented.

Alternative Embodiment 2

Figure 17:
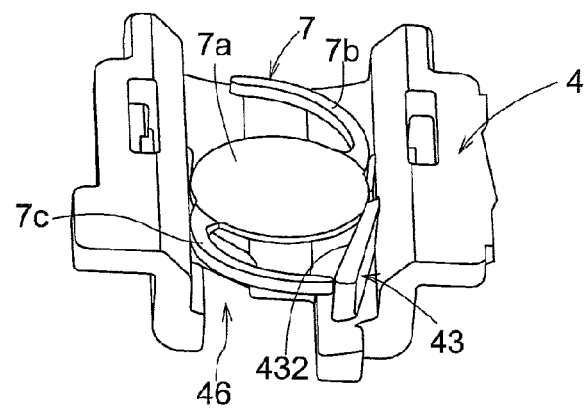
FIG. 17 is a perspective view showing a lens holder in a second alternative embodiment.

As shown in FIG. 17, in the wall portion 43 of the lens holder 4, there is provided a sloped wall portion 432 which extends away from the plunger 5 toward the far side along the push-in direction of the plunger 5.

In order to allow the entire rear haptic 7c to be bent/deformed rather than a local deformation occurs at a portion of the rear haptic 7c when the rear haptic 7c approaches the intraocular lens 7 in association with push-in operation of the plunger 5, it is preferred that the rear haptic 7c as a whole be deformed angularly around the proximal end portion of this rear haptic 7c. In such case, the distal end portion of the rear haptic 7c will move obliquely relative to the push-in direction of the plunger 5, rather than along this push-in direction of the plunger 5.

The sloped wall portion 432 allows the distal end portion of the rear haptic 7c to move obliquely relative to the push-in direction of the plunger 5, so that no unnatural bending will occur in the rear haptic 7c and no inappropriate rotation of the intraocular lens 7 will occur either. Therefore, when the plunger 5 comes into contact with the intraocular lens 7, the distal end portion 51 of the plunger 5 can come into contact with the rear haptic 7c and the optic 7a in a reliable manner.

Incidentally, the sloped wall portion 432 can be provided at a portion of the wall portion 43, by e.g. causing the wall portion 43 to be sloped from its intermediate portion on the far side along the push-in direction of the plunger 5.

Alternative Embodiment 3

Figure 18:
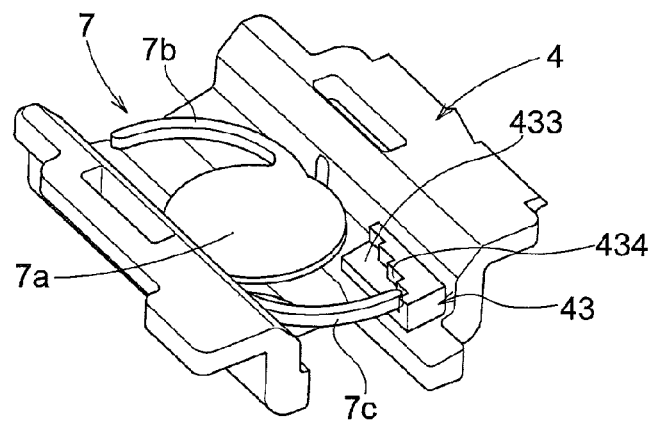
FIG. 18 is a perspective view showing a lens holder in a third alternative embodiment.

As shown in FIG. 18, in the wall portion 43 of the lens holder 4, there can be provided a stepped portion 433 for placing thereon the distal end portion of the rear haptic 7c on the side away from the bottom portion 21 of the device body 2 relative to the thickness-wise center position 71 of the optic 7a and a staircase-like portion 434 extending away from the plunger 5 toward the far side in the push-in direction of the plunger 5.

By the stepped portion 433, during push-in operation of the plunger 5, it is possible to prevent the distal end portion of the rear haptic 7c from being deformed downwards along the thickness direction of the optic 7a. Thus, the contacting condition of the distal end portion 51 of the plunger 5 with the rear haptic 7c can be maintained in a reliable manner. Further, by the staircase-like portion 434, the distal end portion of the rear haptic 7c is caused to move obliquely relative to the push-in direction of the plunger 5, so that no unnatural bending will occur in the rear haptic 7c and no inappropriate rotation of the intraocular lens 7 will occur either. Therefore, when the plunger 5 comes into contact with the intraocular lens 7, the distal end portion 51 of the plunger 5 can come into contact with the rear haptic 7c and the optic 7a in a reliable manner.

Other Embodiments (1) The wall portion 43 can vary in many ways as long as it fixedly determines the direction of movement of the rear haptic 7c by coming into contact with this rear haptic 7c. For instance, though not shown, the wall portion 43 can be configured such that a corner portion thereof on the side away from the bottom portion 21 of the device body 2 relative to the thickness-wise center position 71 of the optic 7a and located on the far side in the push-in direction of the plunger 5 is cut away.

(2) The positioner comprised of the convex portion 24 and the inserting portion 46 can vary in many ways as long as it pushes up the rear haptic 7c within the range contactable with the distal end portion 51 of the plunger 5 and along the thickness direction of the optic 7c.

For instance, in the second embodiment, the convex portion 24 and the inserting portion 46 can be provided such that the wall portion 43 and the convex portion 24 are disposed in juxtaposition when the lens holder 4 is assembled to the device body 2. Further, in the upper end face of the wall portion 43, a sloped face may be provided which extends away from the bottom portion 21 of the device body 2 toward the far side along the push-in direction of the plunger 5, so that the rear haptic 7c may be guided along this sloped face toward the region upwardly of the optic 7a.

(3) Instead of the second convex portion 24b formed on the bottom portion 21 of the device body 2 in the first embodiment and the alternative embodiment 1, it is possible to provide a convex portion which protrudes from the bottom portion 41 of the lens holder 4. Incidentally, in case the intraocular lens 7 is stored for a long time in the lens holder 4, there is possibility of plastic deformation in the rear haptic 7c. Therefore, it is preferred that the intraocular lens 7 be set in the lens holder 4 which is assembled to the device body 2 in advance.

Figure 19:
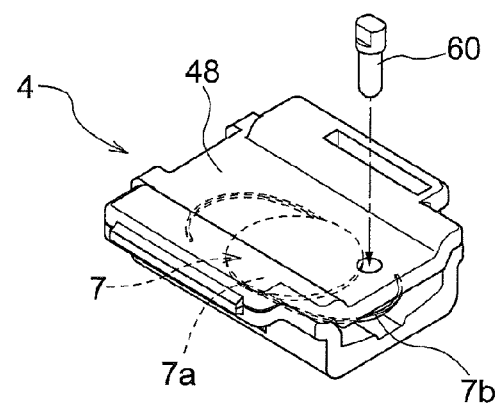
FIG. 19 is a perspective view showing a lens holder in a fourth alternative embodiment.

(4) As an alternative embodiment 4, as shown in FIG. 19, a hole can be provided at a front portion of the lid portion 48 of the lens holder 4 and a regulating pin 60 can be inserted into this hole. As a result, the regulating pin 60 is disposed between the front haptic 7b and the optic 7a of the intraocular lens 7 held in the lens holder 4, thus, inadvertent movement of the intraocular lens 7 can be restricted. In this case, the push-in operation of the plunger 5 will be carried out after removal of the regulating pin 60. Thus, with the push-in operation of the plunger 5, the intraocular lens 7 can be advanced smoothly.

INDUSTRIAL APPLICABILITY

The present invention is applicable to an intraocular lens injector for use in inserting an intraocular lens into an eye.

REFERENCE SIGNS LIST

1: intraocular lens injector
2: device body
21: bottom portion
24: convex portion (positioner)
24a: first convex portion (positioner)
24b: second convex portion (positioner)
32: nozzle portion
4: lens holder
41: bottom portion
43: wall portion (guiding portion)
432: sloped wall portion (guiding portion)
433: stepped portion (guiding portion)
46: inserting portion (positioner)
5: plunger
51: distal end portion
7: intraocular lens
7a: optic
7b: front haptic (haptic)
7c: rear haptic (haptic)
71: center position

The invention claimed is:

1. An intraocular lens injector comprising:
a lens holder holding an intraocular lens which has an optic and a haptic extending in a curved shape from the optic;
a device body to which the lens holder is attached;
a plunger inserted projectably/retractably in the device body and coming into contact with the intraocular lens to push out the intraocular lens;
a nozzle portion connected to the device body, the nozzle portion releasing the intraocular lens while folding the intraocular lens concavely by a push-in operation of the plunger; and
a positioner pushing up the haptic along a thickness direction of the optic within a range contactable with a distal end of the plunger while the optic is mounted on a bottom portion of the lens holder and when the lens holder and the intraocular lens are attached to the device body, the positioner being provided in distribution in the device body and in the lens holder;
wherein the positioner includes a convex portion provided by the device body and protruding from a bottom portion of the device body and having an end face pushing up the haptic at the time of attachment of the lens holder and the intraocular lens to the device body, and an inserting portion provided in the lens holder, wherein the inserting portion is configured to avoid interference with the convex portion.

2. The intraocular lens injector according to claim 1, wherein the lens holder includes a guiding portion coming into contact with the haptic to determine a movement direction of the haptic in the course of the push-in operation of the plunger.

3. The intraocular lens injector according to claim 2, wherein the guiding portion is provided in the form of a wall on a lateral side of the plunger and extending between a position where a distal end portion of the haptic is located under an initial condition of the intraocular lens being attached to the lens holder and a position where the distal end portion of the haptic moves when the plunger is pushed in to come into contact with the intraocular lens.

4. The intraocular lens injector according to claim 3, wherein at least in a portion of the guiding portion, there is provided a sloped wall portion extending progressively away from the plunger toward a far side along a push-in direction of the plunger.

5. The intraocular lens injector according to claim 4, wherein in the guiding portion, there is formed, along a push-in direction of the plunger, a stepped portion by which the distal end portion of the haptic is placed on the side away from the bottom portion of the device body, relative to a thickness-wise center position of the optic.

6. The intraocular lens injector according to claim 3, wherein in the guiding portion, there is formed, along a push-in direction of the plunger, a stepped portion by which the distal end portion of the haptic is placed on the side away from the bottom portion of the device body, relative to a thickness-wise center position of the optic.

7. The intraocular lens injector according to claim 1, wherein the lens holder includes a guiding portion coming into contact with the haptic to determine a movement direction of the haptic in the course of the push-in operation of the plunger.

8. The intraocular lens injector according to claim 7, wherein the guiding portion is provided in the form of a wall on a lateral side of the plunger and extending between a position where a distal end portion of the haptic is located under an initial condition of the intraocular lens being attached to the lens holder and a position where the distal end portion of the haptic moves when the plunger is pushed in to come into contact with the intraocular lens.

9. The intraocular lens injector according to claim 8, wherein at least in a portion of the guiding portion, there is provided a sloped wall portion extending progressively away from the plunger toward a far side along a push-in direction of the plunger.

10. The intraocular lens injector according to claim 9, wherein in the guiding portion, there is formed, along a push-in direction of the plunger, a stepped portion by which the distal end portion of the haptic is placed on the side away from the bottom portion of the device body, relative to a thickness-wise center position of the optic.

11. The intraocular lens injector according to claim 8, wherein in the guiding portion, there is formed, along a push-in direction of the plunger, a stepped portion by which the distal end portion of the haptic is placed on the side away from the bottom portion of the device body, relative to a thickness-wise center position of the optic.

* * * * *